(12) United States Patent
Hayden

(10) Patent No.: US 6,267,728 B1
(45) Date of Patent: Jul. 31, 2001

(54) METHOD FOR EVALUATING ATHEROSCLEROSIS AND ITS AFFECT ON THE ELASTICITY OF ARTERIAL WALLS

(76) Inventor: Steven Mark Hayden, 76297 Tallassee Hwy., Wetumpka, AL (US) 36092

( * ) Notice: Subject to any disclaimer, the term of this patent is extended or adjusted under 35 U.S.C. 154(b) by 0 days.

(21) Appl. No.: 09/339,283

(22) Filed: Jun. 23, 1999

(51) Int. Cl.$^7$ .................................................... A61B 5/02
(52) U.S. Cl. ............................................................ 600/481
(58) Field of Search .................................. 600/481, 454, 600/437, 455

(56) References Cited

U.S. PATENT DOCUMENTS

| | | | | |
|---|---|---|---|---|
| 4,721,113 | * | 1/1988 | Stewart et al. ...................... | 128/661 |
| 5,241,963 | * | 9/1993 | Shankar .............................. | 128/668 |
| 5,297,556 | * | 3/1994 | Shankar .............................. | 128/668 |
| 5,343,867 | * | 9/1994 | Shankar .............................. | 128/668 |
| 5,515,849 | * | 5/1996 | Murashita et al. ................ | 128/660.7 |

* cited by examiner

*Primary Examiner*—Max Hindenburg
*Assistant Examiner*—Brian Szmal

(74) *Attorney, Agent, or Firm*—Robert J. Veal; Burr & Forman LLP

(57) ABSTRACT

A method for evaluating atherosclerosis using M-Mode ultrasound to measure atherosclerotic plaques and their affect on compliance of the arterial walls in peripheral arteries. Movement of the arterial walls is measured during a systolic-diastolic pressure cycle and the intimal medial thickness and the thickness of any atherosclerotic lesions are measured as well. The method measures the distance between the near and far walls of the subject artery and the acoustic impedance of the materials that comprise the individual layers of the arterial walls. To image an artery with M-Mode ultrasound, a transducer head having at least one transmitting element and at least one receiving element is placed against a patient's skin adjacent the peripheral artery to be evaluated. A repeating series of sound pulses are transmitted from the transmitting element into the patient substantially perpendicular to the subject artery. The sound waves are reflected to varying degrees by the tissues encountered and the reflected waves are measured by the receiving element(s) in the transducer head. M-Mode ultrasound allows for continuous monitoring of the position of the arterial walls during the systolic-diastolic pressure cycle such that changes in position of the arterial wall can be measured over a predetermined period of time.

13 Claims, 3 Drawing Sheets

METHOD FOR EVALUATING ATHEROSCLEROSIS AND ITS AFFECT ON THE ELASTICITY OF ARTERIAL WALLS

FIELD OF THE INVENTION

The present invention relates to a method of using ultrasound to evaluate atherosclerosis in arteries. More particularly, the present invention relates to a method of using M-Mode ultrasound to evaluate atherosclerosis in peripheral arteries and its affect on the elasticity of the arterial walls.

BACKGROUND OF THE INVENTION

Atherosclerotic plaques, or lesions, have been known to contribute to the progression of various diseases, including heart attacks, strokes, and peripheral vascular disease, and to the general aging process itself. As atherosclerosis develops and advances in arteries, the arteries become less compliant. One goal in the health care industry has been to diagnose and evaluate atherosclerosis in a cost-effective and non-evasive manner. Presently, B-Mode ultrasound imaging is used to make two-dimensional, cross-sectional representations of an artery, such as the carotid artery. These B-Mode representations provide for visualization of plaques in arterial walls, however, they do not adequately provide for evaluation of any loss of arterial wall compliance. For example, B-Mode representations can be collected and compared over time to show changes to an arterial wall which can indicate loss of arterial wall compliance. Further, the B-Mode representations must be collected and stored over a long period of time, which requires a substantial amount of data storage space and complex software to evaluate these representations.

Accordingly, what is needed is an expedient method for evaluating atherosclerosis and its affect on arterial wall compliance which overcomes the problems found in present non-evasive methods.

SUMMARY OF THE INVENTION

It is an object of the present invention to provide a method for evaluating atherosclerosis in an expedient and non-evasive manner.

It is another object of the present invention to provide a method for evaluating atherosclerosis in peripheral arteries, such as the femoral, popliteal, carotid, and brachial arteries.

It is another object of the present invention to provide a method for evaluating atherosclerosis using M-Mode ultrasound.

It is another object of the present invention to provide a method for evaluating arterial wall compliance by measuring changes in an arterial wall during a systolic-diastolic pressure wave.

These and other objects of the present invention are accomplished through a method for evaluating atherosclerosis using M-Mode ultrasound to measure atherosclerotic plaques and their affect on compliance of the arterial walls in peripheral arteries. Movement of the arterial walls is measured during a systolic-diastolic pressure cycle, which allows for immediate determination of abnormal arterial compliance. M-Mode ultrasound also provides for measurement of intimal medial thickness as well as the thickness of any atherosclerotic lesions. M-Mode ultrasound provides for measurement of the distance between the near and far walls of the subject artery and the acoustic impedance of the materials that comprise the individual layers of the arterial walls.

To image an artery with M-Mode ultrasound, a transducer having at least one transmitting element and at least one receiving element is placed against a patient's skin adjacent the peripheral artery to be evaluated. A repeating series of sound pulses are transmitted from the transmitting element into the patient substantially perpendicular to the subject artery. The sound waves are reflected to varying degrees by the tissues encountered and the reflected waves are collected by the receiving element(s) in the transducer and the collected data is imaged for evaluation. M-Mode ultrasound allows for continuous monitoring of the position of the arterial walls during the systolic-diastolic pressure cycle such that changes in position of the arterial wall can be measured over a predetermined period of time. While M-Mode technology has been available for many years in the medical field, it has been used virtually exclusively for evaluating cardiac measurements and has never been used to evaluate changes in the diameter of arteries during a systolic-diastolic pressure wave.

These and other objects and advantages of the invention will become apparent from the following detailed description of the preferred embodiment of the invention.

BRIEF DESCRIPTION OF THE DRAWINGS

The accompanying drawings form a portion of this disclosure and wherein.

DETAILED DESCRIPTION OF THE PREFERRED EMBODIMENT

Figure 1:
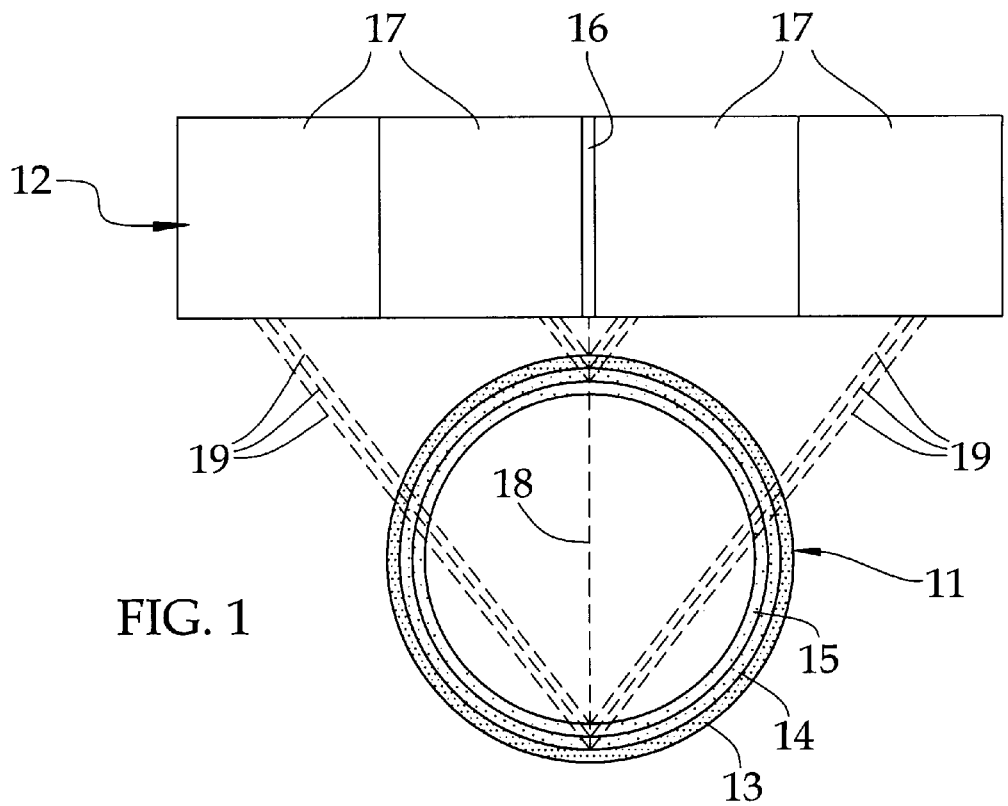
FIG. 1 is a cross-sectional view of sound waves being reflected from an artery having mild atherosclerosis.
Figure 2:
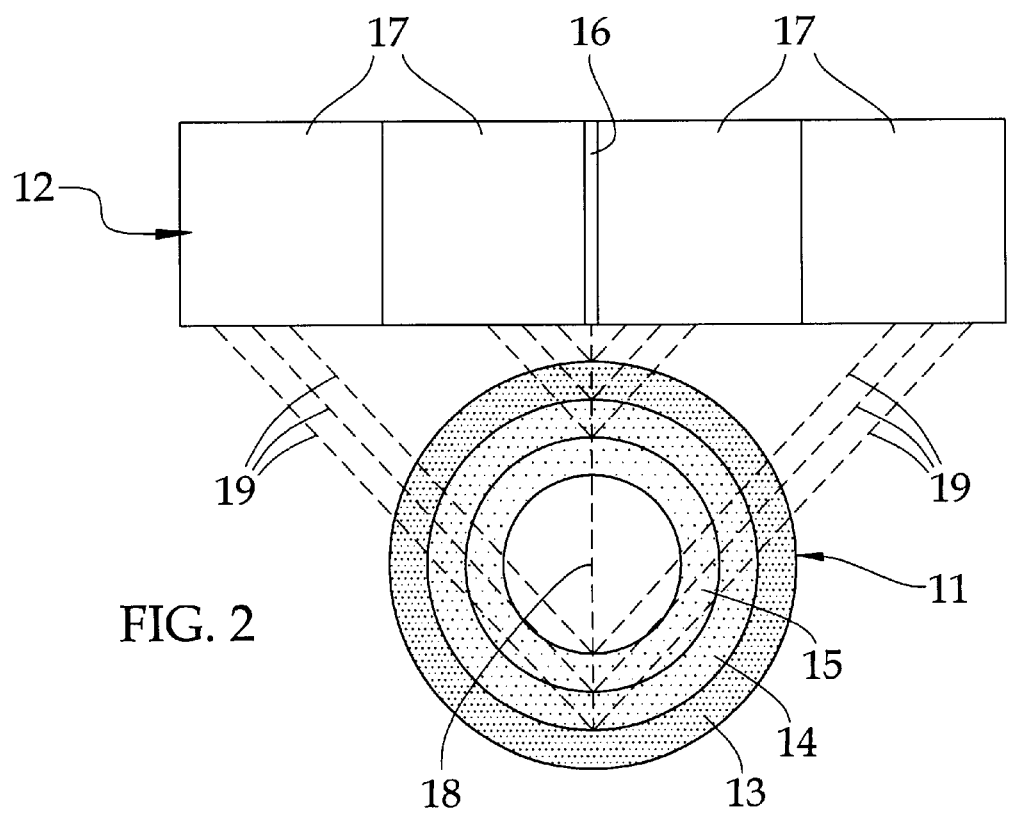
FIG. 2 is a cross-sectional view of sound waves being reflected from an artery having advanced atherosclerosis.
Figure 3:
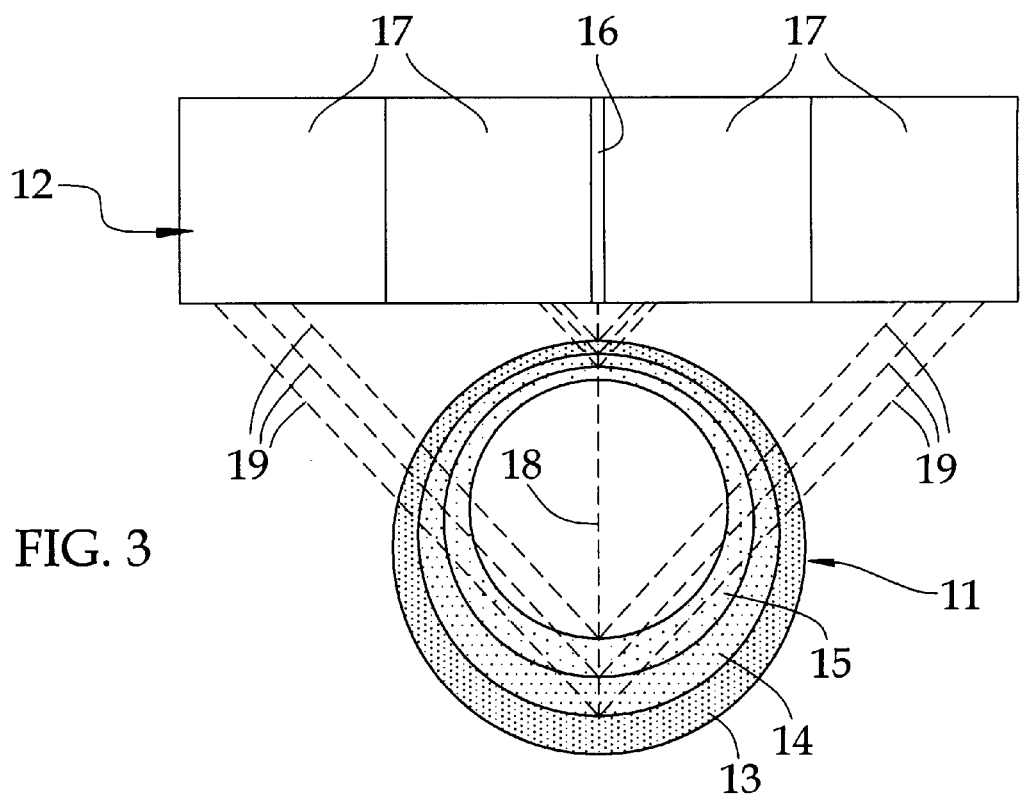
FIG. 3 is a cross-sectional view of sound waves being reflected from an artery having asymmetric atherosclerosis.

The present method uses M-Mode ultrasound to evaluate the distance between the near and far walls of the subject vessel and the acoustic impedance of the materials that comprise the individual layers of the near and far walls of the vessel, with the near wall being defined as the wall closest to the transducer. FIGS. 1–3 illustrate cross-sectional views of arteries 11 having various degrees of atherosclerosis and a transducer 12 adjacent thereto for measuring the compliance of the artery and the thickness of the individual layers thereof. Each artery comprises 3 primary layers: an adventitial layer 13, a muscular layer 14, and an intimal or "fatty" layer 15. The transducer 12 preferably comprises one transmitting element 16 and at least two receiving elements 17, wherein the transducer 12 is connected to a central processing unit (CPU) which controls the intensity and frequency of emitted sound waves 18 from the transmitting element 16 as well as processing of reflected sound waves 19, or echoes, registered by the receiving elements 17. The transmitting element 16 is preferably capable of transmitting and receiving both M-Mode and B-Mode ultrasound for the reasons set forth hereinbelow. Because M-Mode and B-Mode ultrasound and the equipment used to transmit, receive, and process these signals are well known and readily available in the industry, these items will not be discussed in detail herein.

In the method of the present invention, the subject vessel is preferably located using B-Mode ultrasound imaging. Doppler ultrasound may be used to locate small vessels, such as the vertebral arteries in the neck, as well as to document blood flow during the procedure. When a B-Mode image of the vessel is obtained, the CPU is switched to the M-Mode setting. The M-Mode ultrasound allows changes in the vessel wall to be observed during a systolic-diastolic pressure wave cycle. The beam of M-Mode ultrasound should be applied substantially perpendicular to the vessel so that it travels through the longitudinal axis of the vessel.

In FIGS. 1–3, the transmitting element 16 sends a sound wave 18 across the cross-sectional center of the artery 11. The sound wave 18 preferably travels substantially perpendicular through the longitudinal axis of the artery 11. It will initially pass through the outermost adventitial layer 13. The adventitial layer 3 comprises primarily collagen and elastin and some calcium deposits which will cause the sound to be reflected back in the general direction of the transducer 12. However, collagen and elastin tends to be very focused reflectors and if the sound wave is not focused perpendicular to the adventitial layer 13, much of the information will be reflected away from the transducer 12. The reflection from the adventitial layer 13 tends to be a focused reflection, with the sound being focused back at the receiving elements 17.

After the sound wave 18 passes through the adventitial layer 13, it will pass through the muscular layer 14. The muscular layer 14 in most patients at an early age is very thin, but as atherosclerosis develops and elastin fibers are replaced with collagen fibers, the arterial wall tends to lose it elasticity. Elastin fibers tend to be very elastic in nature. However, collagen fibers tend to lose their elasticity. As a result, in order to maximize the elasticity of a given section of an artery, the muscular layer will tend to hypertrophy.

After the sound wave 18 passes through the muscular layer 14, it will pass through the intimal layer 15 of the vessel 11. The intimal layer, or "fatty" layer, can be generated from the atrophy of muscular tissue in the muscular layer 14. The fatty layer 15 is the cause for what is termed "fatty arteries". However, most arteries that have atherosclerosis have more than just fatty lesions, they have hypertrophied muscle and changes in the elastin and collagen layers. Although in many arteries, the lesions are located in an equal pattern circumferentially, some peripheral arteries will have these lesions concentrated in one area or another. The body tries to compensate for any type of loss of elasticity of any particular area by increasing the muscular layer. However, over time such muscular layers may eventually atrophy and produce fatty deposits. The hypertrophy of smooth muscle layers is frequently followed by the development of fatty tissue in these areas. If compensatory mechanisms occur, then the arterial wall will tend to maintain its compliance or elasticity in a given area as long as possible.

These different types of tissues that are encountered by the M-Mode ultrasound beam can be evaluated based on the nature of their reflectivity. Fatty layers tend to scatter the ultrasound beam and reflect the energy in an unfocused fashion. Muscular layers and collagen layers tend to be focused reflectors. Collagen layers and especially calcified collagen layers will tend to be very focused reflectors. Unfortunately, some of the collagen layers will contain calcium crystals which will form in the arterial wall during the inflammatory process when the precipitation of calcium is possible. These calcium crystals will tend to be very focused reflectors. Focused reflectors can be identified from unfocused reflectors because the reflected energy will be more concentrated on a receiving element. Accordingly, the fatty layer 15 can be differentiated from the muscular 14 and adventitial 13 walls.

Figure 4:
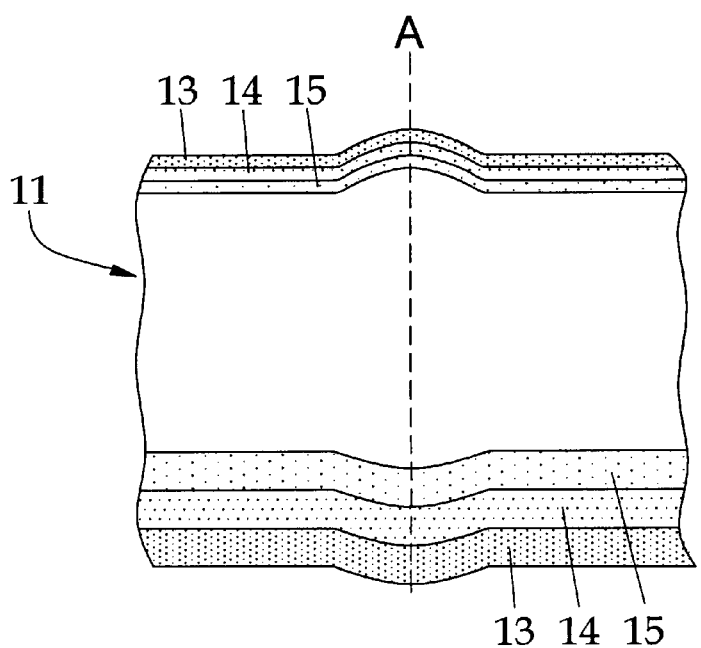
FIG. 4 is a sectional view of a pressure wave traveling through an artery having asymmetric atherosclerosis.

FIGS. 3–4 illustrate an artery 11 having an asymmetric buildup of atherosclerosis and FIG. 4 illustrates a diastolic wave, designated by A, passing through the vessel 11. The fatty 15 and muscular 14 layers in the far wall is much thicker than the near wall. In addition, the adventitial layer 13 in the far wall is much thicker than the near wall due to calcium deposits. The distance between the near and far wall can be measured during a systolic-diastolic cardiac cycle. This can be done using M-Mode measurements when the beam is perpendicular to the adventitial walls. The true thickness of the arterial wall can best be measured by making sure that the ultrasound is directed perpendicular through the arterial wall. If the ultrasound travels at an oblique angle, the wall will seem to be much thicker than it actually is. In addition, much of the reflected sound may not be returned to the receiving elements. It is therefore imperative in this technique that efforts be made to keep the M-Mode beam perpendicular or nearly perpendicular to the wall of the vessel. When the beam is perpendicular to the arterial walls, the near and far walls will tend to move apart from each other during a systolic-diastolic pressure wave cycle. The distance between the near wall and the transducer can be monitored during the cardiac pressure cycle. Movement of this near wall can be recorded using digital instrumentation and measurement along the M-Mode cycle. Movement of the far wall from the transducer can also be measured.

Figure 5:
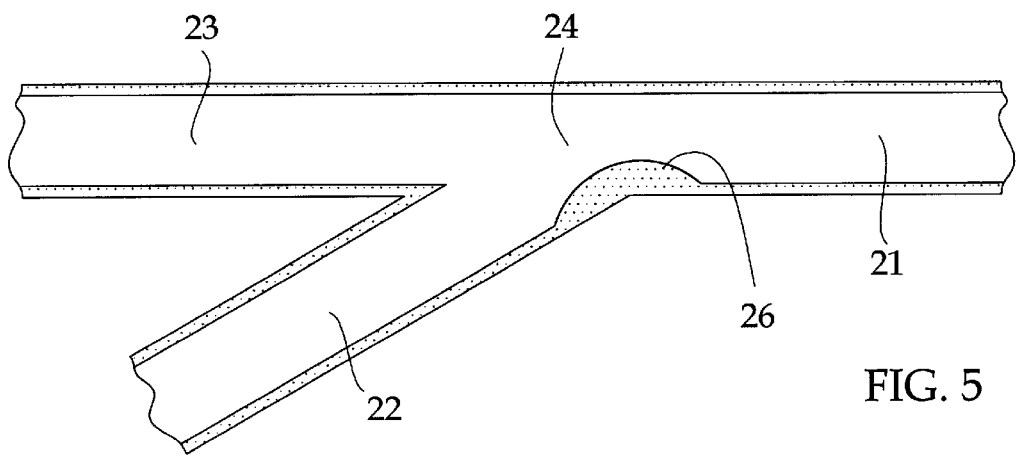
FIG. 5 is a sectional view of an arterial junction having an atherosclerotic plaque therein.

Movement of the near wall is not always equal in magnitude to movement of the far wall due to changes in the rigidity of both the near and the far wall. An example of this is given in FIG. 5, which illustrates the carotid artery bifurcation, which includes the proximal carotid artery 21, the internal carotid artery 22, and the distal external carotid artery 23. The point of bifurcation is termed the carotid bulb 24. Most atherosclerotic lesions 26 initially develop along the carotid bulb 24 or along the origin of the internal carotid artery 22. As atherosclerosis develops, the adventitial wall 13 will tend to thicken and develop calcium deposits. In addition, the fatty layer 15 and muscular layer 14 of the atherosclerotic lesion will increase in thickness. As these lesions develop, the affected area of the arterial wall will become hard and noncompliant. This can cause the opposing wall to become more distended by the systolic wave. What has been observed is that the near wall movement during the systolic phase is greater than expected even though mild atherosclerosis is involved. This is because the displacement of the near wall towards the transducer is possible and the far wall is being held rigidly in place by the lesion 26. As a result, while the overall movement of the opposing walls from each other will increase, the near wall may reflect a much greater amplitude of movement during the systolic wave than the far wall.

When an atherosclerotic lesion tends to occur asymmetrically in a vessel, as shown in FIGS. 3–4, major changes in local compliance can occur. When one part of a tissue of the wall is less compliant than another, the wall will tend to want to separate. In the vasculature of atherosclerotic lesions, atherosclerotic lesions tend to be hard and noncompliant, and when they occur in a portion of the outer circumference of the wall, they tend to cause greater internal stress where these lesions meet the more compliant portions. As a result of the concentration of forces near nonelastic media, tears are possible. When tears occur, you can have an acute rupture of a blood vessel or tearing of the intimal medial complex, resulting in a release of thrombogenic materials that trigger clotting and occlusion of the vessel. Certain patients that have more pronounced movement of the near wall compared to the far wall will have a worse prognosis than patients that have less compliance but equal amounts of near and fall wall movement. When an artery tends to have equal atherosclerotic lesions throughout its surface, as shown in FIGS. 1–2, the lesions tend to be much less focal in nature. These atherosclerotic lesions impart equal stress along the arterial walls. While near and far wall compliance will decrease with age, the near and far wall movement will much more closely parallel each other in their decrease in compliance.

The following technique is recommended for use in evaluating atherosclerosis using M-Mode. The M-Mode can first be shot through the subject artery. The thickness of the different layers can be documented. The beam can be focused either on the near or far wall depending on which wall is being evaluated at a particular time. Focusing the beam on either the near or fall wall will improve the resolution and distinction of the boundaries that separate these layers. The movement of the near and far walls in the artery can be recorded and measured using M-Mode by documenting the movement of both the near and far wall during a complete systolic and diastolic pressure wave cycle.

Figure 6:
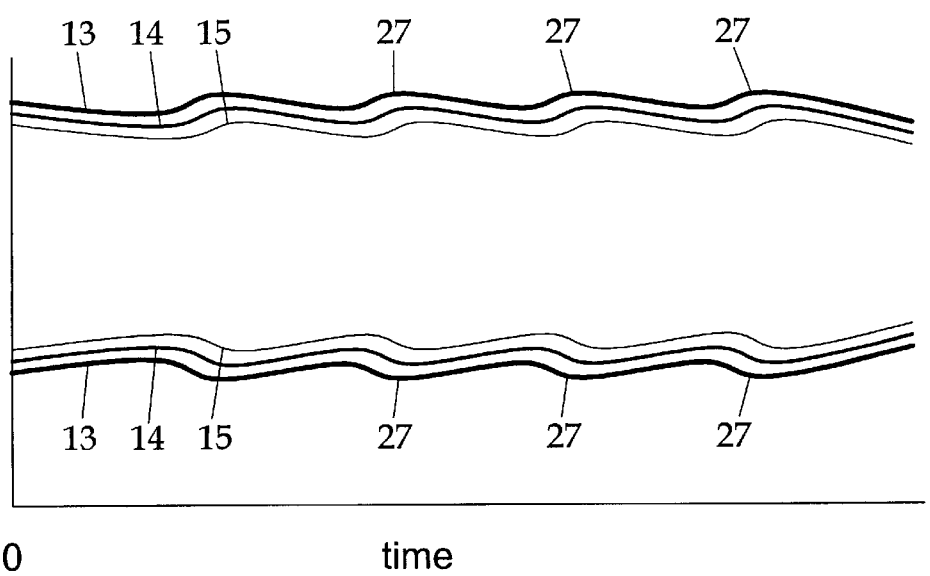
FIG. 6 is an image produced from M-Mode ultrasound waves reflected from various layers of an artery.

The sound echoes received from reflecting tissues typically image as a series of scrolling lines, as shown in FIG. 6, showing the position of the reflecting tissues based on time with the systolic pressure waves indicated at the peaks 27. As that reflecting tissue changes its position in time, it can produce a continuous line or wave. The slope of that wave can be calculated as well as its distance from another reflecting tissue. Useful information includes the slope of the line as well as the overall change in the distance between two separate reflecting tissues in the near and far arterial walls. If the vessel is irregular in shape, an additional measurement using B-Mode imaging can document the width of the vessel. The width of the vessel can be used to determine the stress on the arterial wall at that point. The wall stress can be calculated as the pressure on the inside lumen of the vessel. The stress on a particular portion of the wall can be calculated if you know the systolic blood pressure and the changes in the pressure at that point in the vessel. An estimation of the changes in the pressure of the artery at that point can be done by taking the systolic pressure and subtracting from it the diastolic pressure and measuring the change in the diameter of the vessel during that change in pressure. The arterial wall tends to be composed of a variety of different materials, but it is still possible to measure the change in artery diameter in proportion to the amount of change of systolic minus diastolic pressure. One can generally use the change in the systolic and diastolic pressures that are measured and recorded using a stethoscope and blood pressure cuff at the brachial artery. The change in diameter is a reflection of the amount of increase of pressure during the systolic phase of pressure that is applied to the vessel walls.

B-Mode imaging has difficulties in identifying and visualizing the intimal wall 15 of the arterial vessel 11. This is because the images are produced by reflections from the intimal wall. When the intimal wall has a very small amount of reflection due to fatty deposits, the reflection is sometimes difficult to distinguish between the background echoes that are coming from other tissue areas. The tissue reflections can be confused with scattering, shattering, or echoing from other areas because the fat in the intimal wall has a low-intensity echo compared to calcium deposits. However, the M-Mode can be used to identity whether an echo is moving in response to changes due to pressure. In M-Mode, which documents movement of an echo with time, it is possible to see whether an individual echo reflection is moving with the arterial wall. Almost all arterial walls, even those hardened up with calcium, will show some changes or movement with the increased systolic pressure. The arterial walls move in opposite directions when pressure is applied inside the artery. Accordingly, echoes on the far wall of the artery will move in an opposite direction from the echoes from the near wall of the artery. This supplies additional information that helps determine whether these echoes are from the near or far arterial wall. In this way, M-Mode measurements make possible a more precise or accurate measurement of the intimal wall of the vessel.

The beneficial effect of using M-Mode compared to B-Mode to measure arterial wall is possible only because the arterial wall tends to move or flex with time. It is therefore possible to get a more accurate reflection as to which part of an echo is coming from the near or the far arterial wall based on how that echo is moving on M-Mode. It is recommended that the compliance of the vessel during the systolic phase be calculated based on the cross-sectional width of the vessel. The cross-sectional width of the vessel can be measured by B-Mode or else it can be approximated by the M-Mode. If the center of the vessel or lumen of the vessel is circular, then the distance of the lumen as measured on M-Mode will be identical to the width. The force placed on the arterial wall should be proportional to the cross-sectional area times the change in pressure. The change in pressure is represented as the systolic minus the diastolic pressure.

It is possible to document the EKG simultaneously with the M-Mode. EKG information shows how soon after the contraction of the heart the pressure wave is actually reaching the arterial wall being evaluated. The EKG can be displayed simultaneously and useful information such as when the pulse is actually traveling from the heart to the arterial wall can be obtained. The entire pulse curve produced by movement of the arterial wall can be documented using M-Mode and this pulse curve can document the compliance of the vessel, which is the change in the vessel shape compared to the pressure that is applied to it, and the profile of those changes in pressure that are occurring at the arterial wall. The overall changes in the profile of the pressure curve are affected and influenced by the hardening of the arteries, since harder arteries tend to transmit the pressure more rapidly downstream than arteries that are more compliant. Information in this area can be used to correlate and evaluate the compliance of the vessels between both the site that is being is studied and the site that is producing the arterial pulse, such as the heart. The actual slope of the movement of the arterial wall can be documented and calculated both statistically and software can be developed that will keep track of an individual line or curve on the M-Mode and show the slope of the curve as well as the overall shape and displacement underneath. Studies can be done to analyze the data for best evaluation of atherosclerotic progression and regression as well as evaluation of future heart attack and stroke risks.

It is to be understood that the form of the invention shown is a preferred embodiment thereof and that various changes and modifications may be made therein without departing from the spirit of the invention or scope as defined in the following claims.

Having set forth the nature of the invention, what is claimed is:

1. A method for evaluating atherosclerosis in an artery, comprising the steps of:
   a. locating an artery;
   b. transmitting M-Mode sound waves transversely through the artery such that said sound waves pass through opposing walls of the artery;
   c. detecting M-Mode sound waves reflected from the opposing walls; and
   d. evaluating said detected sound waves to determine the thickness of the opposing walls and diameter of the artery.

2. A method according to claim 1, wherein the artery is located in step (a) using B-Mode sound waves.

3. A method according to claim 1, wherein said M-Mode sound waves are transmitted in step (b) through the longitudinal axis of the artery.

4. A method according to claim 1, wherein steps (a) to (d) are performed during a systolic-diastolic pressure wave cycle.

5. A method according to claim 1, wherein steps (a) to (d) are performed during a time period comprising a plurality of systolic-diastolic pressure wave cycles.

6. A method for measuring thickness of the intimal layer of an arterial wall to evaluate atherosclerosis in an artery, comprising the steps of:
   a. locating an artery;
   b. transmitting M-Mode sound waves transversely through the artery such that said sound waves pass through the intimal layer of an arterial wall;
   c. detecting M-Mode sound waves reflected from the intimal layer; and
   d. evaluating said detected sound waves to determine the thickness of the intimal layer and the degree of atherosclerosis in the artery.

7. A method according to claim 6, wherein the artery is located in step (a) using B-Mode sound waves.

8. A method according to claim 6, wherein said M-Mode sound waves are transmitted in step (b) through the longitudinal axis of the artery.

9. A method according to claim 6, wherein steps (a) to (d) are performed during a systolic-diastolic pressure wave cycle.

10. A method according to claim 6, wherein steps (a) to (d) are performed during a time period comprising a plurality of systolic-diastolic pressure wave cycles.

11. A method for evaluating compliance of an artery, comprising the steps of:
    a. locating an artery;
    b. transmitting M-Mode sound waves through the artery during a time period comprising a plurality of systolic-diastolic pressure wave cycles, wherein said sound waves are transmitted transversely through the longitudinal axis of the artery such that said sound waves pass through opposing walls of the artery;
    c. detecting M-Mode sound waves reflected from the opposing walls; and
    d. evaluating said detected sound waves to determine changes in diameter of the artery during the systolic-diastolic pressure wave cycles.

12. A method according to claim 11, wherein the artery is located in step (a) using B-Mode sound waves.

13. A method according to claim 11, further comprising the step of (e) measuring the time period from a heart contraction to arrival of the corresponding systolic-diastolic pressure wave at a location of detection of said reflected M-Mode sound waves to evaluate compliance of arteries between the heart and the location of detection of said reflected M-Mode sound waves.

* * * * *